US012290233B2

(12) United States Patent
Sasaki

(10) Patent No.: US 12,290,233 B2
(45) Date of Patent: May 6, 2025

(54) INFORMATION PROCESSING DEVICE AND GENERATION METHOD

(71) Applicant: SONY GROUP CORPORATION, Tokyo (JP)

(72) Inventor: Toshiyuki Sasaki, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 409 days.

(21) Appl. No.: 17/755,681

(22) PCT Filed: Nov. 11, 2020

(86) PCT No.: PCT/JP2020/042089

§ 371 (c)(1),
(2) Date: May 5, 2022

(87) PCT Pub. No.: WO2021/095773

PCT Pub. Date: May 20, 2021

(65) Prior Publication Data

US 2022/0378278 A1 Dec. 1, 2022

(30) Foreign Application Priority Data

Nov. 14, 2019 (JP) ................................ 2019-205950

(51) Int. Cl.

| | |
|---|---|
| ***A61B 1/00*** | (2006.01) |
| ***A61B 1/045*** | (2006.01) |
| ***G06T 5/40*** | (2006.01) |
| ***H04N 19/51*** | (2014.01) |

(52) U.S. Cl.

CPC ........ *A61B 1/000095* (2022.02); *A61B 1/045* (2013.01); *G06T 5/40* (2013.01); *H04N 19/51* (2014.11)

(58) Field of Classification Search

None

See application file for complete search history.

(56) References Cited

U.S. PATENT DOCUMENTS

| | | | |
|---|---|---|---|
| 2011/0064280 | A1 | 3/2011 | Sasakawa |
| 2018/0061029 | A1 | 3/2018 | Suzuki |
| 2019/0059696 | A1 | 2/2019 | Hirayama et al. |

(Continued)

FOREIGN PATENT DOCUMENTS

| | | | |
|---|---|---|---|
| JP | 11-318909 | A | 11/1999 |
| JP | 2016-158886 | A | 9/2016 |
| JP | 2017-158776 | A | 9/2017 |

(Continued)

OTHER PUBLICATIONS

International Search Report and Written Opinion of PCT Application No. PCT/JP2020/042089, issued on Dec. 15, 2020, 08 pages of ISRWO.

(Continued)

*Primary Examiner* — Kyle Zhai

(74) *Attorney, Agent, or Firm* — CHIP LAW GROUP

(57) ABSTRACT

A generation unit that generates an output image by correcting a first image based on deterioration of the first image due to a substance generated during surgery estimated based on the first image that is an image regarding surgery and a second image that is an image prior to the first image is included.

11 Claims, 8 Drawing Sheets

(56) References Cited

U.S. PATENT DOCUMENTS

| | | | | |
|---|---|---|---|---|
| 2020/0022687 | A1 | 1/2020 | Takemoto et al. | |
| 2024/0046415 | A1 * | 2/2024 | Gan | H04N 23/86 |

FOREIGN PATENT DOCUMENTS

| | | | |
|---|---|---|---|
| JP | 2018-157917 | A | 10/2018 |
| WO | WO-2018084003 | A1 | 5/2018 |
| WO | WO-2018163644 | A1 | 9/2018 |

OTHER PUBLICATIONS

Kopf, et al., "Joint Bilateral Upsampling", ACM Transactions on Graphics, (ToG), vol. 26, No. 3, 2007, 5 pages.

He, et al., "Guided Image Filtering", IEEE, Transactions on Pattern Analysis and Machine Intelligence, vol. 35, No. 6, Jun. 2013, 14 pages.

Gastal, et al., "Domain Transform for Edge-Aware Image and Video Processing", ACM Transactions on Graphics, (ToG), vol. 30, No. 4, Article 69, Jul. 2011, 12 pages.

* cited by examiner

CCU
LIGHT SOURCE DEVICE
ARM CONTROL DEVICE
INPUT DEVICE
TREATMENT TOOL CONTROL DEVICE
SMOKE ELIMINATION DEVICE
RECORDER
PRINTER

ENDOSCOPE
5115
IMAGE-CAPTURING DEVICE
10
IMAGE-CAPTURING UNIT
11
COMMUNICA-TION UNIT
12
TREATMENT TOOL CONTROL DEVICE
5163
DEVICE USAGE MONITORING DEVICE
20
MONITORING UNIT
21
COMMUNICA-TION UNIT
22
30
DISPLAY DEVICE
5155
CCU
5153
INFORMATION PROCESSING DEVICE
100

INFORMATION PROCESSING DEVICE
100
USAGE DEVICE INFORMATION
SELECTION UNIT
102
MEMORY
101b
MOTION COMPENSA-TION UNIT
104
HISTOGRAM CONVER-SION UNIT
103
MEMORY
101a
DETERIORATION ESTIMATION UNIT
105
HISTOGRAM CONVER-SION UNIT
105a
CORRECTION MAP CALCU-LATION UNIT
105b
CORRECTION MAP FORMA-TION UNIT
105c
GENERATION UNIT
106
OUTPUT IMAGE
INPUT IMAGE

INFORMATION PROCESSING DEVICE AND GENERATION METHOD

CROSS REFERENCE TO RELATED APPLICATIONS

This application is a U.S. National Phase of International Patent Application No. PCT/JP2020/042089 filed on Nov. 11, 2020, which claims priority benefit of Japanese Patent Application No. JP 2019-205950 filed in the Japan Patent Office on Nov. 14, 2019. Each of the above-referenced applications is hereby incorporated herein by reference in its entirety.

FIELD

The present disclosure relates to an information processing device, a generation method, and a generation program.

BACKGROUND

In medical sites, endoscopic surgery using an endoscope is widely performed. In addition, various devices related to endoscopic surgery have been developed. For example, Patent Literature 1 discloses a device that operates a pneumoperitoneum device to remove smoke when smoke is detected from a captured endoscopic image.

Patent Literature 2 discloses a device that, upon detecting smoke from a captured endoscopic image, removes the smoke from the endoscopic image by uniform signal processing, and then controls a smoke elimination device according to a detection result of the smoke to remove the smoke.

CITATION LIST

Patent Literature

Patent Literature 1: JP H11-318909 A
Patent Literature 2: JP 2018-157917 A

SUMMARY

Technical Problem

However, in Patent Literature 1, even when the presence or absence of smoke is detected, the amount of smoke is not detected, and depending on the amount of smoke generated, there is a case where the smoke cannot be sufficiently removed. In addition, in Patent Literature 1, since smoke is physically removed, it takes time until the smoke is discharged and the visual field becomes clear.

In addition, in Patent Literature 2, since smoke is detected from one endoscopic image, in a case where a subject similar to the color of smoke appears in the endoscopic image, it is difficult to distinguish between the subject and the smoke, and an image as a result of removing the smoke may be deteriorated due to erroneous detection of the smoke.

Therefore, the present disclosure proposes an information processing device, a generation method, and a generation program that can generate an image in which deterioration due to a substance occurring during surgery is corrected.

Solution to Problem

To solve the problems described above, an information processing device according to an embodiment of the present disclosure includes: a generation unit that generates an output image by correcting a first image based on deterioration of the first image due to a substance generated during surgery estimated based on the first image that is an image regarding surgery and a second image that is an image prior to the first image.

DESCRIPTION OF EMBODIMENTS

Figure 1:
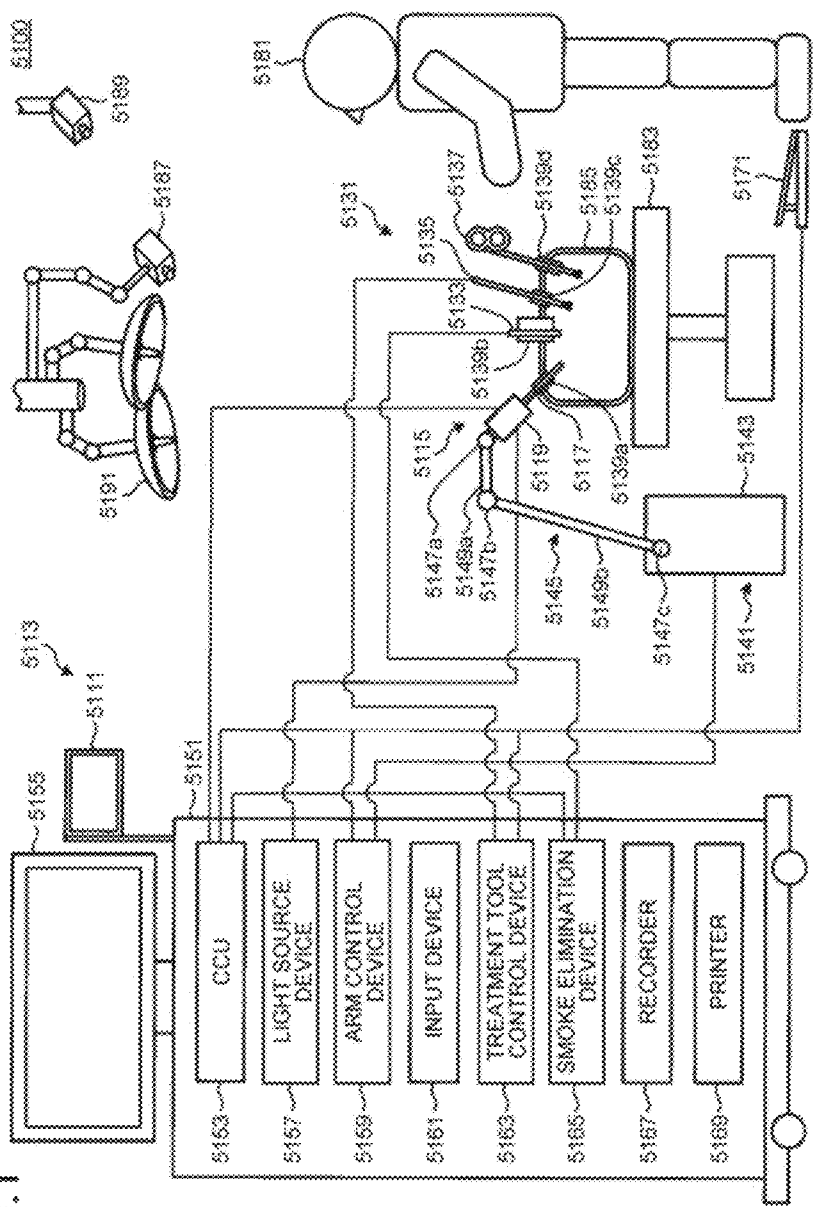
FIG. 1 is a view illustrating an example of a situation of surgery to which an operation room system using a technical idea according to the present disclosure is applied.

Embodiments of the present disclosure will be described in detail below with reference to the drawings. In each embodiment below, the same parts are given the same reference numerals, and redundant description will be omitted.

In addition, the present disclosure will be described according to the following item order.

1. Application example
2. Embodiments
2.1. Configuration of system according to embodiment
2.2. Configuration of information processing device according to embodiment
2.3. Flow of operation of information processing device
2.4. Effects of information processing device according to embodiment
3. Hardware configuration
4. Conclusions

1. APPLICATION EXAMPLE

Application examples of the technical idea common to each embodiment of the present disclosure will be described. FIG. 1 is a view illustrating an example of a situation of surgery to which an operation room system 5100 using the technical idea according to the present disclosure is applied. A ceiling camera 5187 and an operation room camera 5189 are provided on the ceiling of the operation room, and can photograph the hands of an operator (doctor) 5181 who performs treatment on an affected part of a patient 5185 on a patient bed 5183 and the situation of the entire operation room. The ceiling camera 5187 and the operation room camera 5189 can be provided with a magnification adjustment function, a focal length adjustment function, a photographing direction adjustment function, and the like. An illumination 5191 is provided on the ceiling of the operation room and illuminates at least the hands of the operator 5181. The illumination 5191 may be appropriately adjustable of the irradiation light amount, the wavelength (color) of the irradiation light, the irradiation direction of the light, and the like.

An endoscopic surgery system 5113, the patient bed 5183, the ceiling camera 5187, the operation room camera 5189, and the illumination 5191 are connected to be able to cooperate with one another via an audiovisual controller and an operation room control device (not illustrated). A centralized operation panel 5111 is provided in the operation room, and the user can appropriately operate these devices existing in the operation room via the centralized operation panel 5111.

Hereinafter, the configuration of the endoscopic surgery system 5113 will be described in detail. As illustrated, the endoscopic surgery system 5113 includes an endoscope 5115, other surgical tools 5131, a support arm device 5141 that supports the endoscope 5115, and a cart 5151 on which various devices for endoscopic surgery are mounted.

In endoscopic surgery, instead of cutting the abdominal wall for laparotomy, a plurality of cylindrical apertura instruments called trocars 5139*a* to 5139*d* are punctured into the abdominal wall. Then, a lens barrel 5117 of the endoscope 5115 and the other surgical tools 5131 are inserted into the body cavity of the patient 5185 from the trocars 5139*a* to 5139*d*. In the illustrated example, as the other surgical tools 5131, a tube 5133, an energy treatment tool 5135, and a forceps 5137 are inserted into the body cavity of the patient 5185. Here, the tube 5133 may be configured to eliminate the smoke generated in the body cavity to the outside of the body cavity. On the other hand, the tube 5133 may have a function of injecting gas into the body holder to inflate the body cavity. Furthermore, the energy treatment tool 5135 is a treatment tool that performs incision and dissection of tissue, sealing of a blood vessel, or the like by high-frequency current or ultrasonic vibration. However, the illustrated surgical tools 5131 are merely examples, and various surgical tools generally used in endoscopic surgery such as tweezers and a retractor may be used as the surgical tools 5131.

An image of the surgical site in the body cavity of the patient 5185 photographed by the endoscope 5115 is displayed on a display device 5155. While viewing in real time the image of the surgical site displayed on the display device 5155, the operator 5181 performs treatment such as resection of the affected part using the energy treatment tool 5135 and the forceps 5137. Note that although not illustrated, the tube 5133, the energy treatment tool 5135, and the forceps 5137 are supported by the operator 5181, an assistant, or the like during surgery.

(Support Arm Device)

The support arm device 5141 includes an arm part 5145 extending from a base part 5143. In the illustrated example, the arm part 5145 includes joint parts 5147*a*, 5147*b*, and 5147*c* and links 5149*a* and 5149*b*, and is driven under the control of an arm control device 5159. The endoscope 5115 is supported by the arm part 5145, and its position and posture are controlled. This makes it possible to achieve stable fixation of the position of the endoscope 5115.

(Endoscope)

The endoscope 5115 includes a lens barrel 5117 whose region of a predetermined length from the tip end is inserted into the body cavity of the patient 5185, and a camera head 5119 connected to the base end of the lens barrel 5117. In the illustrated example, the endoscope 5115 configured as a so-called rigid scope including the rigid lens barrel 5117 is illustrated, but the endoscope 5115 may be configured as a so-called flexible endoscope including the flexible lens barrel 5117.

An opening part into which an objective lens is fitted is provided at the tip end of the lens barrel 5117. A light source device 5157 is connected to the endoscope 5115. The light generated by the light source device 5157 is guided to the tip end of the lens barrel 5117 by a light guide extending inside the lens barrel, and is emitted toward an observation target in the body cavity of the patient 5185 via the objective lens. Note that the endoscope 5115 may be a forward-viewing endoscope, an oblique-viewing endoscope, or a side-viewing endoscope.

An optical system and an image-capturing element are provided inside the camera head 5119, and reflected light (observation light) from the observation target is condensed on the image-capturing element by the optical system. The observation light is photoelectrically converted by the image-capturing element, and an electric signal corresponding to the observation light, that is, an image signal corresponding to the observation image is generated. The image signal is transmitted to a camera control unit (CCU) 5153 as RAW data. Note that the camera head 5119 has a function of adjusting the magnification and the focal length by appropriately driving the optical system.

Note that, for example, in order to be compatible with stereoscopic viewing (3D display) or the like, the camera head 5119 may be provided with a plurality of image-capturing elements. In this case, a plurality of relay optical systems are provided inside the lens barrel 5117 in order to guide the observation light to each of the plurality of image-capturing elements.

(Various Devices Mounted on Cart)

The CCU 5153 includes a central processing unit (CPU) and a graphics processing unit (GPU), and integrally controls operations of the endoscope 5115 and the display device 5155. Specifically, the CCU 5153 performs, on the image signal received from the camera head 5119, various types of image processing for displaying an image based on the image signal such as development processing (demosaic processing) for example. The CCU 5153 provides the display device 5155 with an image signal subjected to the image processing. Furthermore, the audiovisual controller described above is connected to the CCU 5153. The CCU 5153 also provides the audiovisual controller 5107 with an image signal subjected to image processing. Furthermore, the CCU 5153 transmits a control signal to the camera head 5119 and controls drive of the camera head 5119. The control signal can include information regarding image capturing conditions such as magnification and focal length. The information regarding the image capturing conditions may be input via an input device 5161 or may be input via the centralized operation panel 5111 described above.

The display device 5155 displays an image based on the image signal subjected to the image processing by the CCU 5153 under the control of the CCU 5153. In a case where the endoscope 5115 is compatible with high-resolution photographing such as 4K (3840 horizontal pixels×2160 vertical pixels) or 8K (7680 horizontal pixels×4320 vertical pixels), and/or in a case where the endoscope 5115 is compatible with 3D display, for example, a display device capable of high-resolution display and/or a display device capable of 3D display can be used as the display device 5155 corresponding to the respective cases. In a case where the display device is compatible with high-resolution photographing such as 4K or 8K, a further immersive feeling is available by using the display device 5155 having a size of 55 inches or larger. Furthermore, a plurality of the display devices 5155 having different resolutions and sizes may be provided depending on the application.

The light source device 5157 includes a light source such as a light emitting diode (LED), for example, and supplies irradiation light for photographing the surgical site to the endoscope 5115.

The arm control device 5159 includes a processor such as a CPU, for example, and operates according to a predetermined program, thereby controlling driving of the arm part 5145 of the support arm device 5141 in accordance with a predetermined control method.

The input device 5161 is an input interface for the endoscopic surgery system 5113. The user can input various types of information and instructions to the endoscopic surgery system 5113 via the input device 5161. For example, the user inputs various types of information regarding surgery, such as physical information of a patient and information regarding a surgical procedure of the surgery, via the input device 5161. Furthermore, for example, the user inputs an instruction to drive the arm part 5145, an instruction to change image capturing conditions (type of irradiation light, magnification, focal length, and the like) by the endoscope 5115, an instruction to drive the energy treatment tool 5135, and the like via the input device 5161.

The type of the input device 5161 is not limited, and the input device 5161 may be various known input devices. As the input device 5161, for example, a mouse, a keyboard, a touchscreen, a switch, a foot switch 5171, and/or a lever can be applied. In a case where a touchscreen is used as the input device 5161, the touchscreen may be provided on the display surface of the display device 5155.

Alternatively, the input device 5161 is a device worn by the user such as, for example, a glasses-type wearable device or a head mounted display (HMD), and various inputs are performed in accordance with a gesture or a line of sight of the user detected by these devices. Furthermore, the input device 5161 includes a camera capable of detecting motion of the user, and various inputs are performed in accordance with a gesture or a line of sight of the user detected from an image captured by the camera. Furthermore, the input device 5161 includes a microphone capable of collecting a user's voice, and various inputs are performed by voice via the microphone. As described above, the input device 5161 is configured to be able to input various types of information in a non-contact manner, and thus, in particular, a user (e.g., the operator 5181) belonging to a clean area can operate equipment belonging to an unclean area in a non-contact manner. In addition, since the user can operate the equipment without releasing his/her hand from the surgical tool he/she has, the convenience of the user is improved.

A treatment tool control device 5163 controls driving of the energy treatment tool 5135 for cauterization of a tissue, incision, sealing of a blood vessel, or the like. A smoke elimination device 5165 feeds gas into the body cavity of the patient 5185 via the tube 5133 in order to inflate the body cavity for the purpose of securing a visual field by the endoscope 5115 and securing a working space of the operator. In addition, the smoke elimination device 5165 has a function of eliminating gas generated in the body cavity in order to secure a visual field by the endoscope 5115. A recorder 5167 is a device capable of recording various types of information regarding surgery. A printer 5169 is a device capable of printing various types of information regarding surgery in various formats such as text, image, or graph.

Hereinafter, a particularly characteristic configuration in the endoscopic surgery system 5113 will be described in more detail.

(Support Arm Device)

The support arm device 5141 includes a base part 5143 and the arm part 5145 extending from the base part 5143. In the illustrated example, the arm part 5145 includes the plurality of joint parts 5147*a*, 5147*b*, and 5147*c* and the plurality of links 5149*a* and 5149*b* coupled by the joint part 5147*b*. However, FIG. 1 illustrates the configuration of the arm part 5145 in a simplified manner for the sake of simplicity. Actually, the shape, number, and arrangement of the joint parts 5147*a* to 5147*c* and the links 5149*a* and 5149*b*, the directions of the rotation axes of the joint parts 5147*a* to 5147*c*, and the like can be appropriately set so that the arm part 5145 has a desired degree of freedom. For example, the arm part 5145 can be suitably configured to have 6 or more degrees of freedom. As a result, since the endoscope 5115 can be freely moved within the movable range of the arm part 5145, the lens barrel 5117 of the endoscope 5115 can be inserted into the body cavity of the patient 5185 from a desired direction.

Actuators are provided in the joint parts 5147*a* to 5147*c*, and the joint parts 5147*a* to 5147*c* are configured to be rotatable around a predetermined rotation axis by driving of the actuators. The driving of the actuator is controlled by the arm control device 5159, thereby controlling the rotation angle of each of the joint parts 5147*a* to 5147*c*, and controlling the driving of the arm part 5145. As a result, control of the position and posture of the endoscope 5115 can be achieved. At this time, the arm control device 5159 can control the driving of the arm part 5145 by various known control methods such as force control or position control.

For example, by the operator 5181 appropriately performing an operation input via the input device 5161 (including the foot switch 5171), the driving of the arm part 5145 may be appropriately controlled by the arm control device 5159 according to the operation input, and the position and posture of the endoscope 5115 may be controlled. With this control, the endoscope 5115 at the tip end of the arm part 5145 can be moved from an arbitrary position to an arbitrary position and then fixedly supported at the position after the movement. Note that the arm part 5145 may be operated by a so-called master-slave method. In this case, the arm part 5145 can be remotely operated by the user via the input device 5161 installed at a place away from the operation room.

Furthermore, in a case where the force control is applied, the arm control device 5159 may perform so-called power assist control of receiving an external force from the user and driving the actuator of each of the joint parts 5147*a* to 5147*c* so that the arm part 5145 smoothly moves according to the external force. As a result, when the user moves the arm part 5145 while directly touching the arm part 5145, it is possible to move the arm part 5145 with a relatively light force. Therefore, it is possible to more intuitively move the endoscope 5115 with a simpler operation, and it is possible to improve the convenience of the user.

Here, in general, in endoscopic surgery, the endoscope 5115 is supported by a medical doctor called a scopist. On the other hand, by using the support arm device 5141, it is possible to more reliably fix the position of the endoscope 5115 without relying on a manual operation, so that it is possible to stably obtain an image of the surgical site and smoothly perform the surgery.

Note that the arm control device 5159 is not necessarily provided in the cart 5151. Furthermore, the arm control device 5159 is not necessarily one device. For example, the arm control device 5159 may be provided in each of the joint parts 5147*a* to 5147*c* of the arm part 5145 of the support arm device 5141, and the drive control of the arm part 5145 may be achieved by the plurality of arm control devices 5159 cooperating with one another.

(Light Source Device)

The light source device 5157 supplies the endoscope 5115 with irradiation light for photographing the surgical site. The light source device 5157 includes, for example, an LED, a laser light source, or a white light source including a combination thereof. At this time, in a case where the white light source is configured by a combination of RGB laser light sources, the output intensity and the output timing of each color (each wavelength) can be controlled with high accuracy, so that the white balance of the captured image can be adjusted in the light source device 5157. Furthermore, in this case, by irradiating the observation target with the laser light from each of the RGB laser light sources in a time division manner and controlling the driving of the image-capturing element of the camera head 5119 in synchronization with the irradiation timing, it is also possible to capture an image corresponding to each RGB in a time division manner. This method enables a color image to be obtained without providing a color filter in the image-capturing element.

Furthermore, the driving of the light source device 5157 may be controlled so as to change, for each predetermined time, the intensity of light to be output. By controlling the driving of the image-capturing element of the camera head 5119 in synchronization with the timing of the change of the light intensity, acquiring images in a time division manner, and synthesizing the images, it is possible to generate an image of a high dynamic range free from so-called blocked up shadows and blown out highlights.

Furthermore, the light source device 5157 may be configured to be able to supply light in a predetermined wavelength band corresponding to special light observation. In the special light observation, for example, so-called narrow band imaging is performed, in which a predetermined tissue such as a blood vessel in a mucosal surface layer is photographed with high contrast by using wavelength dependency of light absorption in a body tissue and irradiating light in a narrower band than that of irradiation light at the time of normal observation (i.e., white light). Alternatively, in the special light observation, fluorescence observation for obtaining an image by fluorescence generated by irradiation with excitation light may be performed. In the fluorescence observation, fluorescence from a body tissue can be observed by irradiating the body tissue with excitation light (autofluorescence observation), or a fluorescent image can be obtained by locally injecting a reagent such as indocyanine green (ICG) into a body tissue and irradiating the body tissue with excitation light corresponding to a fluorescence wavelength of the reagent. The light source device 5157 can be configured to be able to supply narrow band light and/or excitation light corresponding to such special light observation.

2. EMBODIMENTS

2.1. Configuration of System According to Embodiment

Figure 2:
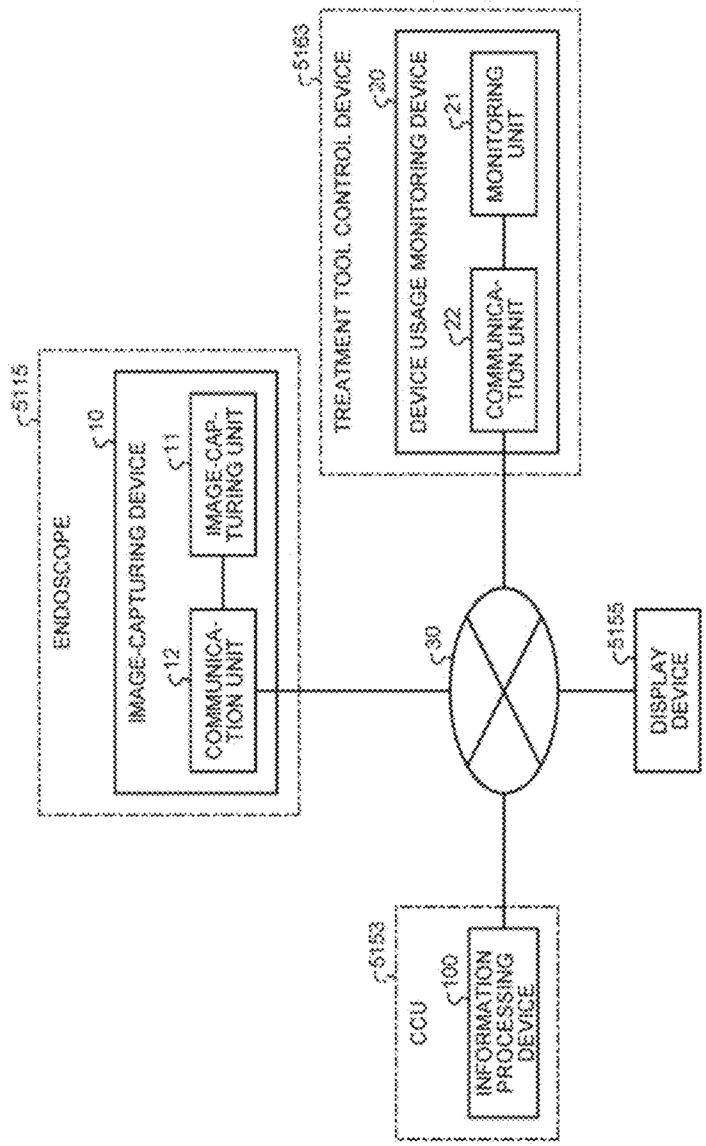
FIG. 2 is a view illustrating a system configuration example according to an embodiment of the present disclosure.

Next, embodiments of the present disclosure will be described in detail. FIG. 2 is a view illustrating the system configuration example according to an embodiment of the present disclosure. As illustrated in FIG. 2, this system includes an image-capturing device 10, a device usage monitoring device 20, a display device 5155, and an information processing device 100. The image-capturing device 10, the device usage monitoring device 20, the display device 5155, and the information processing device 100 are interconnected via a network 30.

The image-capturing device 10 is a device that captures an in-vivo image in a living body of an observation target. The image-capturing device 10 may be the endoscope 5115 as described in FIG. 1, for example. The image-capturing device 10 includes an image-capturing unit 11 and a communication unit 12.

The image-capturing unit 11 has a function of capturing an in-vivo image in a living body of the observation target. The image-capturing unit 11 according to the present embodiment includes an image-capturing element such as a charge coupled device (CCD) or a complementary MOS (CMOS), for example. The image-capturing unit 11 captures an in-vivo image at a predetermined frame rate (frames per second (FPS)).

Here, the in-vivo image according to the present embodiment widely includes images (biological imaging) acquired from a biological viewpoint for clinical, medical, and experimental purposes, and the image-capturing target is not limited to humans.

The communication unit 12 has a function of performing information communications with the information processing device 100 via a network 20. For example, the communication unit 12 transmits each in-vivo image captured by the image-capturing unit 11 to the information processing device 100 in time series.

The device usage monitoring device 20 is a device that is connected to an electrocautery, an ultrasonic coagulation incision device, or the like (not illustrated) and monitors whether or not the electrocautery or the ultrasonic coagulation incision device is used. The device usage monitoring device 20 may be the treatment tool control device 5163 described in FIG. 1, for example. The device usage monitoring device 20 includes a monitoring unit 21 and a communication unit 22.

The monitoring unit 21 is a processing unit that monitors the usage status of the electrocautery and the ultrasonic coagulation incision device. When receiving a control signal for starting use from a use start button of the electrocautery, the ultrasonic coagulation incision device, or the like, for example, the monitoring unit 21 determines that the electrocautery or the ultrasonic coagulation incision device is in use. The monitoring unit 21 generates usage device information. The usage device information includes information on whether or not the electrocautery is in use and information on whether or not the ultrasonic coagulation incision device is in use.

For example, the electrocautery performs hemostasis or incision on an affected part of the patient 5185 by heat generated by a high-frequency current. The electrocautery has a feature of easily generating smoke because it burns the treatment part.

The ultrasonic coagulation incision device coagulates or incises the affected part of the patient 5185 by friction caused by ultrasonic vibration. The ultrasonic coagulation incision device is characterized in that mist is easily generated by ultrasonic vibration.

The information processing device 100 receives each in-vivo image in time series from the image-capturing device 10. In the following description, the in-vivo image received from the image-capturing device 10 is referred to as an "input image". The information processing device 100 estimates deterioration of an input image by a substance generated during surgery based on an image not including smoke and the input image. The information processing device 100 generates an output image based on the estimation result of the deterioration of the input image and the input image. For example, supplies generated during surgery are smoke and mist. The input image is also referred to as a "medical image" or an "intraoperative image".

The information processing device 100 transmits the output image to the display device 5155. As described later, in a case where the input image includes smoke, the information processing device 100 generates an output image excluding smoke. The information processing device 100 may be the CCU 5153 as described with reference to FIG. 1, for example.

The display device 5155 receives an output image from the information processing device 100 and displays the received output image. Other descriptions on the display device 5155 are similar to those on the display device 5155 in FIG. 1.

2.2. Configuration of Information Processing Device According to Embodiment

Figure 3:
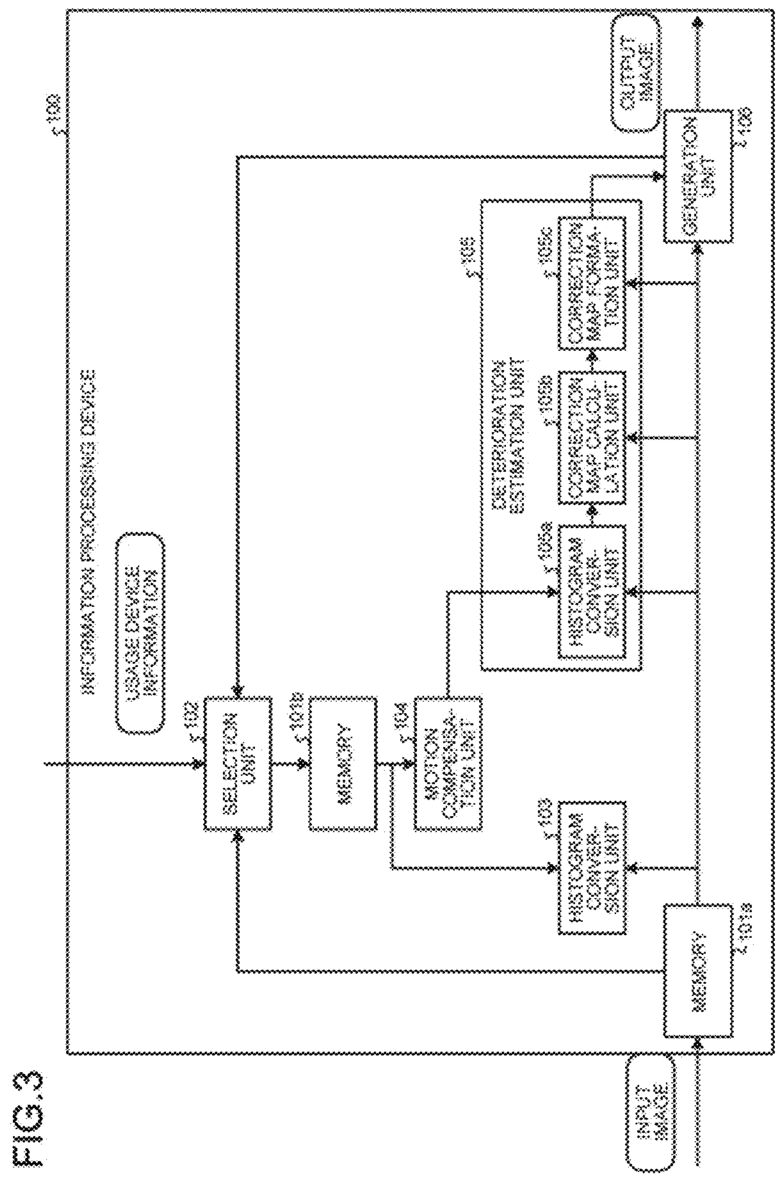
FIG. 3 is a view illustrating a configuration example of an information processing device according to an embodiment of the present disclosure.

Next, the information processing device 100 according to the first embodiment of the present disclosure will be described in detail. FIG. 3 is a view illustrating a configuration example of the information processing device according to an embodiment of the present disclosure. As illustrated in FIG. 3, this information processing device 100 includes memories 101*a* and 101*b*, a selection unit 102, a histogram conversion unit 103, a motion compensation unit 104, a deterioration estimation unit 105, and a generation unit 106. Although not illustrated in FIG. 3, the information processing device 100 includes a communication unit that performs information communications with the image-capturing device 10, the device usage monitoring device 20, and the display device 5155 via the network 30.

((Memory 101*a*))

The memory 101*a* is a storage device that stores, in time series, input images received from the image-capturing device 10. The input image is an example of a "first image". For example, it is assumed that the input images in the memory 101*a* are assigned with frame numbers in ascending order, and the input images up to the frame number n are stored. The memory 101*a* corresponds to a semiconductor memory element such as a random access memory (RAM) or a flash memory, or a storage device such as a hard disk drive (HDD). The memory 101*a* may be either a volatile memory or a nonvolatile memory, or both of them may be used.

((Memory 101*b*))

The memory 101*b* is a storage device that stores a pre-deterioration image selected by the selection unit 102. When storing a past pre-deterioration image, the memory 101*b* updates the past pre-deterioration image with a newly selected pre-deterioration image. The memory 101*b* corresponds to a semiconductor memory element such as a RAM or a flash memory, or a storage device such as an HDD. The memory 101*b* may be either a volatile memory or a nonvolatile memory, or both of them may be used.

((Selection Unit 102))

The selection unit 102 is a processing unit that selects an input image stored in the memory 101*a* or an output image output from the generation unit 106 based on the usage device information received from the device usage monitoring device 20. The selection unit 102 stores the selected image into the memory 101*b*. The image selected by the selection unit 102 is a "pre-deterioration image" in which no smoke or mist has been generated in the image. The pre-deterioration image is an example of a "second image".

Based on the usage device information, the selection unit 102 selects the output image output from the generation unit 106 in a case where either the electrocautery or the ultrasonic coagulation incision device is in use, and stores the selected pre-deterioration image (output image) into the memory 101*b*.

Based on the usage device information, the selection unit 102 selects an input image of the frame number n−1 stored in the memory 101*a* in a case where the electrocautery and the ultrasonic coagulation incision device are not in use, and stores the selected pre-deterioration image (input image) into the memory 101*b*.

Figure 4:
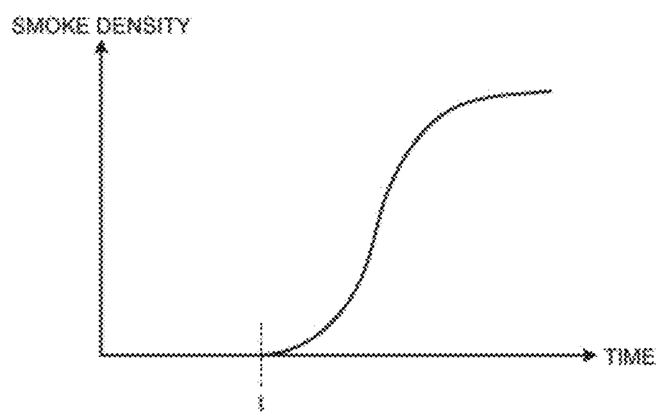
FIG. 4 is a view illustrating a relationship between usage time of an electronic device and concentration of smoke.

FIG. 4 is a view illustrating the relationship between usage time of the electronic device and concentration of smoke. The vertical axis in FIG. 4 is an axis corresponding to the smoke density. The horizontal axis is an axis corresponding to time. In the example illustrated in FIG. 4, the time at which use of the electronic device is started is referred to as time t. The longer the duration of use of the electronic device becomes, the denser the smoke becomes.

While the smoke density is low, the selection unit 102 may select an input image stored in the memory 101*a* and store the selected pre-deterioration image (input image) into the memory 101*b* even when either the electrocautery or the ultrasonic coagulation incision device is in use. For example, the selection unit 102 receives each piece of usage device information in time series, and selects an input image stored in the memory 101*a* for a predetermined time from the time when either the electrocautery or the ultrasonic coagulation incision device is in use first, and stores the selected input image in the memory 101*b*.

((Histogram Conversion Unit 103))

The histogram conversion unit 103 acquires the latest input image (input image with the frame number n) from the memory 101*a* and acquires a pre-deterioration image from the memory 101*b*. In the description of the histogram conversion unit 103, the pre-deterioration image is referred to as a "target image". The histogram conversion unit 103 converts the pixel values of the input image such that the histogram $h_S(s_j)$ of the input image matches the histogram $h_T(t_j)$ of the target image.

Here, $s_j$ represents a j-th pixel value in the input image. $t_j$ indicates a j-th pixel value in the target image. For example, pixel values of the input image and the target image take values from 0 to 255 inclusive. The input image after conversion is referred to as a "histogram converted image". The histogram conversion unit 103 outputs a histogram converted image to the motion compensation unit 104.

Figure 5:
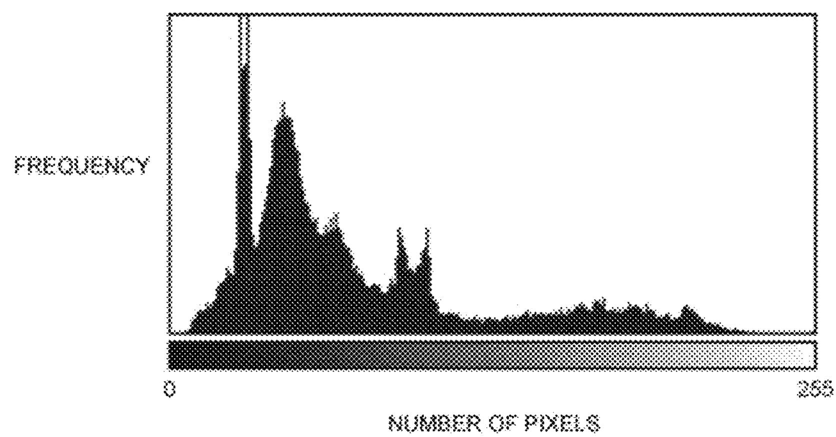
FIG. 5 is a view illustrating an example of a histogram.

FIG. 5 is a view illustrating an example of a histogram. The vertical axis in FIG. 5 is an axis corresponding to the frequency. The horizontal axis is an axis corresponding to the pixel value.

Hereinafter, processing of the histogram conversion unit 103 will be described in detail. The histogram conversion unit 103 obtains a probability density function by normalizing the histogram with the number of pixels. For example, the probability density function $p_S(s_j)$ of the input image is defined by Expression (1). The histogram conversion unit 103 calculates the probability density function $p_S(s_j)$ of the input image based on Expression (1).

$$p_s(s_j) = \frac{h_S(s_j)}{\sum_j h_S(s_j)} \quad (1)$$

A probability density function $p_T(t_j)$ of the target image is defined by Expression (2). The histogram conversion unit 103 calculates the probability density function $p_T(t_j)$ based on Expression (2).

$$p_T(t_j) = \frac{h_T(t_j)}{\sum_j h_T(t_j)} \quad (2)$$

After obtaining the probability density function, the histogram conversion unit 103 obtains a cumulative distribution function of the probability density function. For example, a cumulative distribution function $F_S(s_k)$ of the input image is defined by Expression (3). The histogram conversion unit 103 calculates the cumulative distribution function $F_S(s_k)$ based on Expression (3). In a case where the pixel value of the input image takes a value from 0 to 255 inclusive, k=255.

$$F_S(s_k) = \sum_{j=0}^{k} p_S(s_j) \quad (3)$$

A cumulative distribution function $F_T(t_k)$ of the target image is defined by Expression (4). The histogram conversion unit 103 calculates the cumulative distribution function $F_T(t_k)$ based on Expression (4). In a case where the pixel value of the target image takes a value from 0 to 255 inclusive, k=255.

$$F_T(t_k) = \sum_{j=0}^{k} p_T(t_j) \quad (4)$$

Figure 6:
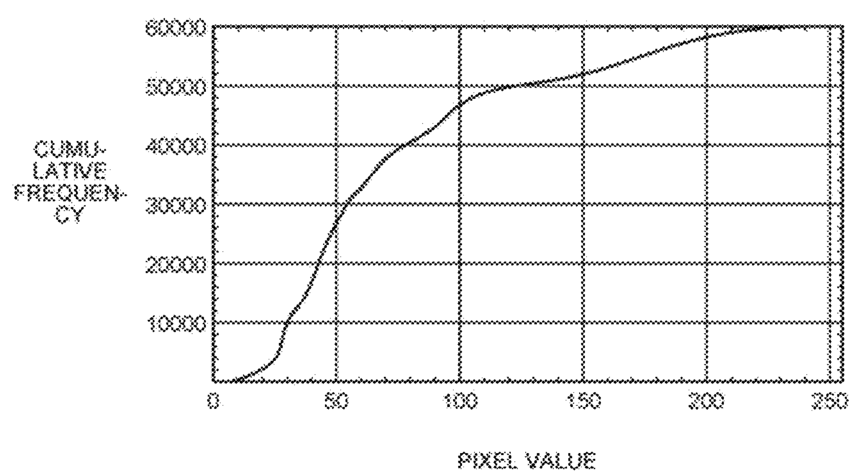
FIG. 6 is a view illustrating an example of a cumulative histogram.

The cumulative distribution function of an image (input image or target image) indicates a cumulative histogram in the image. FIG. 6 is a view illustrating an example of a cumulative histogram. The vertical axis in FIG. 6 is an axis corresponding to the cumulative frequency. The horizontal axis is an axis corresponding to the pixel value. For example, the cumulative frequency corresponding to a pixel value $s_j$ is obtained by accumulating the frequencies of the pixel values $s_0$ to $s_j$.

The histogram conversion unit 103 calculates an inverse function $F_T^{-1}(s_k)$ of $F_T(s_k)$, and converts each pixel value of the input image such that $F_S(s_k)=F_T(s_k)$. For example, the histogram conversion unit 103 generates a histogram converted image H(I) by converting each pixel value $s_j$ (j=0 to 255) of the input image into an output pixel value $o_f$ based on Expression (5).

$$O_j=F_T^{-1}[F_S(s_j)] \quad (5)$$

Here, the histogram conversion unit 103 does not necessarily have to perform the above-described histogram conversion processing on the entire image, and may perform the histogram conversion processing on a specific region of the image or in units of grids.

((Motion Compensation Unit 104))

The motion compensation unit 104 is a processing unit that performs alignment of the pre-deterioration image based on the histogram converted image and the pre-deterioration image. For example, the histogram converted image is an image converted from the input image with the frame number n. The pre-deterioration image is an image corresponding to the input image with the frame number n−1 or the output image based on the input image with the frame number n−1.

The motion compensation unit 104 compares the histogram converted image with the pre-deterioration image, and executes motion vector estimation (ME). In addition, the motion compensation unit 104 executes motion compensation (MC) based on the result of the motion vector estimation to align the position of the subject in the pre-deterioration image to the position of the subject in the histogram converted image.

The motion compensation unit 104 outputs the pre-deterioration image subjected to the alignment to the deterioration estimation unit 105. Note that the motion compensation unit 104 may execute ME and MC using a technique disclosed in JP 2009-295029 A and the like.

((Deterioration Estimation Unit 105))

The deterioration estimation unit 105 acquires the pre-deterioration image subjected to the alignment from the motion compensation unit 104, and acquires the latest input image (input image with the frame number n) from the memory 101*a*. In the description of the deterioration estimation unit 105, the pre-deterioration image subjected to the alignment is simply referred to as a pre-deterioration image. The deterioration estimation unit 105 is a processing unit that estimates deterioration of an input image due to smoke (or mist) generated during surgery based on the pre-deterioration image and the input image. The deterioration estimation unit 105 outputs the estimation result to the generation unit 106.

The deterioration estimation unit 105 includes a histogram conversion unit 105*a*, a correction map calculation unit 105*b*, and a correction map formation unit 105*c*. Hereinafter, the histogram conversion unit 105*a*, the correction map calculation unit 105*b*, and the correction map formation unit 105*c* will be described in order.

((Histogram Conversion Unit 105*a*))

The histogram conversion unit 105*a* acquires the latest input image (input image with the frame number n) from the memory 101*a*, and acquires the pre-deterioration image from the motion compensation unit 104. The histogram conversion unit 105*a* generates a histogram converted image by converting the pixel value of the input image such that the histogram $h_S(s_j)$ of the input image matches the histogram $h_T(t_j)$ of the target image (pre-deterioration image). The histogram conversion unit 105*a* outputs the histogram converted image H(I) to the correction map calculation unit 105*b*.

The processing in which the histogram conversion unit 105*a* generates a histogram converted image based on the input image and the target image is similar to the processing of the histogram conversion unit 103, and therefore the description thereof will be omitted.

((Correction Map Calculation Unit 105*b*))

The correction map calculation unit 105*b* calculates a correction amount map M based on Expression (6). As shown in Expression (6), the correction map calculation unit 105*b* calculates the correction amount map M of contrast by calculating the difference between the histogram converted image H(I) and an input image I.

$$M=H(I)-I \quad (6)$$

The correction map calculation unit **105*b* may calculate the correction amount map M using the physical model of haze. For example, the correction map calculation unit 105*b*** calculates the correction amount map M based on Expression (7). In Expression (7), the maximum pixel value among the pixel values in the input image is set as A.

$$M=(I-A)/(H(I)-A) \quad (7)$$

It is assumed to be set in advance as to whether the correction map calculation unit **105*b*** calculates the correction amount map M using Expression (6) or calculates the correction amount map M using Expression (7).

((Correction Map Formation Unit **105*c***))

The correction map formation unit **105*c*** generates a formed correction amount map F (I, M) by forming the correction amount map with a guided filter using the input image as a guide image. The formed correction amount map F (I, M) is obtained by forming the correction amount map M in accordance with the edge of the input image I. By using the formed correction amount map F (I, M) in this manner, it is possible to prevent image deterioration around the edge that can occur when the positions of the correction amount map M and the input image I are misaligned.

Note that the correction map formation unit **105*c*** may generate the formed correction amount map F (I, M) using a guided filter described in any of Non Patent Literatures 1, 2, and 3 described below.

Non Patent Literature 1: Kopf, Johannes, et al. "Joint bilateral upsampling." ACM Transactions on Graphics (ToG). Vol. 26. No. 3. ACM, 2007.

Non Patent Literature 2: He, Kaiming, Jian Sun, and Xiaoou Tang. "Guided image filtering." European conference on computer vision. Springer, Berlin, Heidelberg, 2010.

Non Patent Literature 3: Gastal, Eduardo SL, and Manuel M. Oliveira. "Domain transform for edge-aware image and video processing." ACM Transactions on Graphics (ToG). Vol. 30. No. 4. ACM, 2011.

The correction map formation unit **105*c* outputs the formed correction amount map F (I, M) to the generation unit 106** as a deterioration estimation result. For example, in the formed correction amount map F (I, M), a pixel value of each pixel is defined.

((Generation Unit 106))

The generation unit 106 is a processing unit that generates an output image by correcting an input image based on a deterioration estimation result. The generation unit 106 outputs the output image to the display device 5155. In addition, the generation unit 106 outputs the output image to the selection unit 102.

In a case where the correction map M is calculated based on Expression (6), the generation unit 106 generates an output image O based on Expression (8). Expression (8) means that processing of adding the pixel values of the pixels at the same position in the formed correction amount map F (I, M) to the pixel values of the pixels of the input image I is executed for each pixel.

$$O=F(I,M)+I \quad (8)$$

On the other hand, in a case where the correction map M is calculated based on Expression (7), the generation unit 106 generates an output image based on Expression (9).

$$O-(I-A)/F(I,M)+A \quad (9)$$

The selection unit 102, the histogram conversion unit 103, the motion compensation unit 104, the deterioration estimation unit 105, and the generation unit 106 described above repeatedly execute the above processing each time a new input image is stored in the memory **101*a***.

Figure 7:
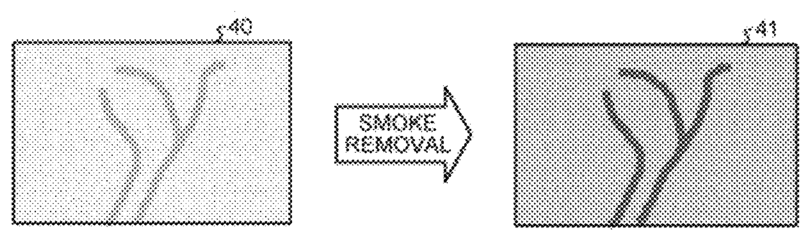
FIG. 7 is a view illustrating an example of an input image and an output image.

FIG. 7 is a view illustrating an example of the input image and the output image. In FIG. 7, in an input image 40, smoke is generated, and a part where the smoke is generated is reflected by light, and transmittance decreases. Therefore, the entire part becomes whitish, and contrast of the background decreases. The information processing device 100 executes the above-described processing on the input image 40, thereby generating an output image 41. In the output image 41, the contrast returns to the original state, and the image becomes clear.

2.3. Flow of Operation of Information Processing Device 100

Figure 8:
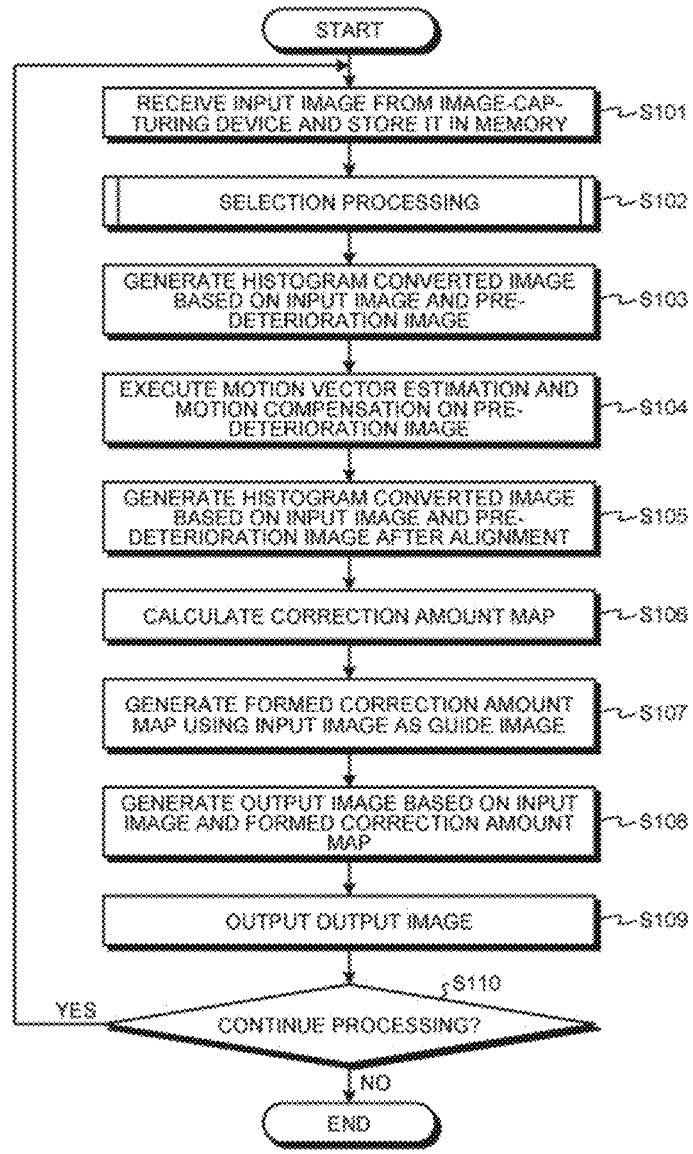
FIG. 8 is a flowchart illustrating a flow of basic operation of the information processing device according to the embodiment of the present disclosure.

Next, the flow of the operation of the information processing device 100 according to the embodiment of the present disclosure will be described. FIG. 8 is a flowchart illustrating the flow of basic operation of the information processing device according to the embodiment of the present disclosure.

In FIG. 8, the information processing device 100 receives an input image from the image-capturing device 10 and stores the input image in the memory **101*a* (step S101). The selection unit 102 of the information processing device 100 executes selection processing (step S102**).

The histogram conversion unit 103 of the information processing device 100 generates a histogram converted image based on the input image and the pre-deterioration image (step S103). The motion compensation unit 104 of the information processing device 100 performs motion vector estimation (ME) and motion compensation (MC) on the pre-deterioration image (step S104).

The deterioration estimation unit 105 (histogram conversion unit **105*a*) of the information processing device 100 generates a histogram converted image based on the input image and the pre-deterioration image after the alignment (step S105). The deterioration estimation unit 105 (correction map calculation unit 105*b*) calculates the correction amount map (step S106**).

The deterioration estimation unit 105 (correction map formation unit **105*c*) generates a formed correction amount map using the input image as a guide image (step S107). The generation unit 106 generates an output image based on the input image and the formed correction amount map (step S108). The generation unit 106 outputs the output image to display device 5155 (step S109**).

In a case where the information processing device 100 continues the processing (step S110, Yes), the processing proceeds to step S101. On the other hand, in a case where the information processing device 100 does not continue the processing (step S110, No), the processing ends.

Figure 9:
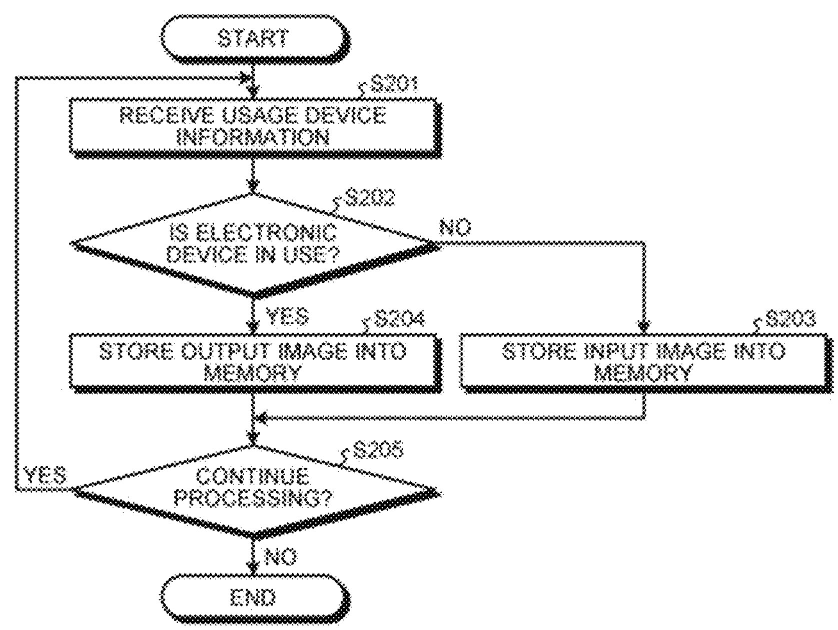
FIG. 9 is a flowchart illustrating a flow of operation of a selection unit according to the embodiment of the present disclosure.

Next, the flow of the operation of the selection process illustrated in step S102 of FIG. 8 will be described. FIG. 9 is a flowchart illustrating the flow of operation of the selection unit according to the embodiment of the present disclosure.

The selection unit 102 of the information processing device 100 receives usage device information from the device usage monitoring device 20 (step S201). The selection unit 102 determines whether or not the electronic device is in use (step S202).

When the electronic device is not in use (step S202, No), the selection unit 102 stores the input image into the memory **101*b* (step S203), and the processing proceeds to step S205. On the other hand, when the electronic device is in use (step S202, Yes), the selection unit 102 stores the output image into the memory 101***b* (step S204).

In a case where the information processing device 100 continues the processing (step S205, Yes), the processing proceeds to step S201. On the other hand, in a case where the information processing device 100 does not continue the processing (step S205, No), the selection processing ends.

2.4. Effects of Information Processing Device According to Embodiment

According to the information processing device 100 according to the first embodiment of the present disclosure, based on a pre-deterioration image and an input image that is an intraoperative image, deterioration of the input image due to generation of smoke is estimated, and an output image is generated based on an estimation result and the input image. This makes it possible to correct the input image deteriorated by smoke in real time.

According to the information processing device 100, since deterioration is estimated by comparing the input image with the pre-deterioration image, even in a case where a subject similar to the color of smoke exists in the endoscopic image, the subject and the smoke can be distinguished from each other, and an output image not affected by the subject color can be generated.

According to the information processing device 100, the histogram converted image in which the pixel value of the input image is converted is generated so that the histogram of the input image matches the histogram of the pre-deterioration image, and the correction amount map is calculated based on the histogram converted image and the input image. This makes it possible to accurately calculate the correction map even if the input image and the pre-deterioration image are misaligned by about a dozen pixels. This is because the histogram is a feature amount that has no phase information and is robust against misalignment.

According to the information processing device 100, based on the operation status of the electronic device, one of the input image of the memory 101*a* and the output image of the generation unit 106 is selected and stored in the memory 101*b*. Thus, use of the operation status of the device makes it possible to more appropriately select the pre-deterioration image in which no smoke has been generated.

The pre-deterioration image stored in the memory 101*b* is the previous image of the input image that becomes a current correction target (the input image or the output image obtained by correcting the input image). Therefore, the time difference between the pre-deterioration image to be compared and the input image can be reduced, and the image quality deterioration of the output image can be prevented.

According to the information processing device 100, processing of forming the correction amount map using the input image as a guide image is executed. This makes it possible to reduce image quality deterioration around the edge that can occur when the correction amount map is calculated in a situation where the input image and the pre-deterioration image are misaligned by about a few dozen pixels.

According to the information processing device 100, after the input image is converted into the histogram converted image, the histogram converted image and the pre-deterioration image are compared and motion compensation is performed. As a result, the alignment can be performed in a state where the contrast of the input image is restored to some extent, and the alignment can be accurately performed even when the deterioration degree of the contrast of the input image is large.

3. HARDWARE CONFIGURATION

Figure 10:
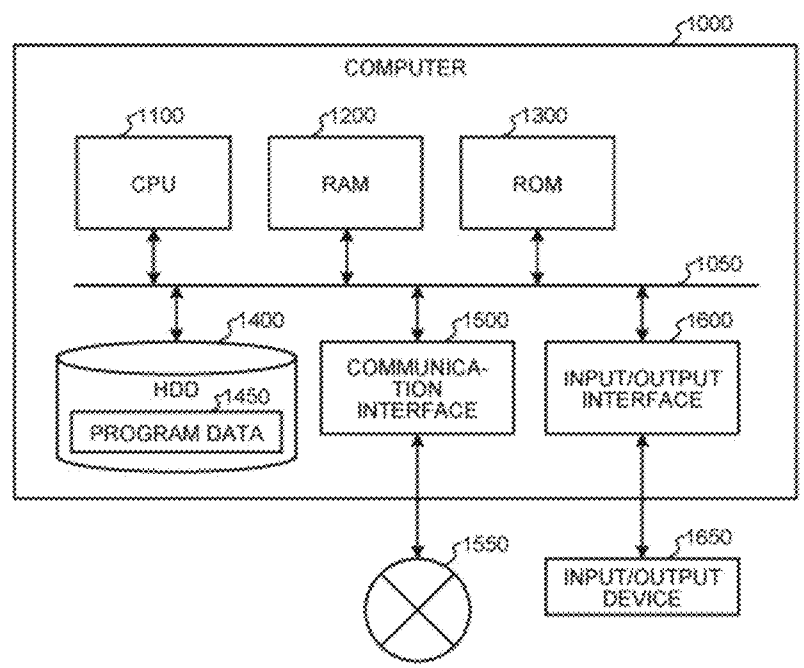
FIG. 10 is a hardware configuration diagram illustrating an example of a computer that implements functions of the information processing device.

The information processing device according to each embodiment described above is achieved by a computer 1000 having a configuration as illustrated in FIG. 10, for example. Hereinafter, the information processing device 100 according to the first embodiment will be described as an example. FIG. 10 is a hardware configuration diagram illustrating an example of the computer 1000 that implements the functions of the information processing device. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates based on a program stored in the ROM 1300 or the HDD 1400, and controls each unit. For example, the CPU 1100 loads a program stored in the ROM 1300 or the HDD 1400 into the RAM 1200, and executes processing corresponding to various programs.

The ROM 1300 stores a boot program such as a basic input output system (BIOS) executed by the CPU 1100 at the start of the computer 1000, a program depending on hardware of the computer 1000, and the like.

The HDD 1400 is a computer-readable recording medium that non-transiently records a program executed by the CPU 1100, data used by the program, and the like. Specifically, the HDD 1400 is a recording medium that records an information processing program according to the present disclosure, which is an example of program data 1450.

The communication interface 1500 is an interface for the computer 1000 to connect to an external network 1550 (e.g., the Internet). For example, the CPU 1100 receives data from another device and transmits data generated by the CPU 1100 to another device via the communication interface 1500.

The input/output interface 1600 is an interface for connecting an input/output device 1650 and the computer 1000. For example, the CPU 1100 receives data from input devices such as a keyboard and a mouse via the input/output interface 1600. In addition, the CPU 1100 transmits data to output devices such as a display, a speaker, or a printer via the input/output interface 1600. Furthermore, the input/output interface 1600 may function as a media interface that reads a program and the like recorded in a predetermined recording medium (media). The media are, for example, an optical recording media such as a digital versatile disc (DVD) and a phase change rewritable disk (PD), a magneto-optical recording media such as a magneto-optical disk (MO), a tape media, a magnetic recording media, a semiconductor memory, and the like.

For example, when the computer 1000 functions as the information processing device 100 according to the embodiment, the CPU 1100 of the computer 1000 executes the information processing program loaded on the RAM 1200, thereby implementing the functions of the selection unit 102, the histogram conversion unit 103, the motion compensation unit 104, the deterioration estimation unit 105, the generation unit 106, and the like. In addition, the HDD 1400 stores a generation program and the like according to the present disclosure. Note that the CPU 1100 reads and executes the program data 1450 from the HDD 1400, but as another example, these programs may be acquired from another device via the external network 1550.

4. CONCLUSIONS

The information processing device includes the generation unit. The generation unit generates an output image by correcting a first image based on deterioration of the first image due to a substance generated during surgery estimated based on the first image that is an image regarding the surgery and a second image that is an image prior to the first image. The generation unit corrects the first image based on deterioration of the first image due to smoke estimated based on the first image and the second image. This makes it possible to correct the input image deteriorated by smoke in real time.

The generation unit corrects the first image based on deterioration estimated based on a past first image in which no smoke is generated or the second image that is a past output image generated by the generation unit and the first image. As a result, even in a case where a subject whose color is similar to the color of smoke exists in the endoscopic image, the subject and the smoke can be distinguished from each other, and an output image not affected by the subject color can be generated.

The information processing device further includes an estimation unit. Based on the first image and the second image, the estimation unit estimates deterioration of the first image due to a substance generated during the surgery. The generation unit generates an output image by correcting the first image based on an estimation result by the estimation unit. The estimation unit generates a converted image in which a pixel value of the first image is converted such that a histogram of the first image matches a histogram of the second image, and calculates a correction amount map based on the converted image and the first image. This makes it possible to accurately calculate the correction map even if the first image and the second image are misaligned by about a dozen pixels. This is because the histogram is a feature amount that has no phase information and is robust against misalignment.

The generation unit generates the output image based on the first image and the correction amount map. The estimation unit calculates the difference between the converted image and the first image as the correction amount map. The estimation unit calculates the correction amount map based on a maximum pixel value among pixel values included in the first image, the converted image, and the first image. The estimation unit further executes processing of forming the correction amount map using the first image as a guide image. This makes it possible to reduce image quality deterioration around the edge that can occur when the correction amount map is calculated in a situation where the first image and the second image are misaligned by about a few dozen pixels.

The image processing device further includes a motion compensation unit that estimates a motion vector based on the first image and the second image and executes motion compensation on the second image based on an estimated motion vector to align the second image, in which the estimation unit generates a converted image in which a pixel value of the first image is converted so as to match a histogram of the aligned second image. The image processing device further includes a histogram conversion unit that generates a converted image in which a pixel value of the first image is converted so that a histogram of the first image matches a histogram of the second image, in which the motion compensation unit aligns the second image by estimating a motion vector based on the converted image and the second image, and executing motion compensation on the second image based on an estimated motion vector. As a result, the alignment can be performed in a state where the contrast of the first image is restored to some extent, and the alignment can be accurately performed even when the deterioration degree of the contrast of the first image is large.

The information processing device further includes a selection unit that selects one of a past output image or a past first image generated by the generation unit as a second image based on an operation status of an electronic device connected to the information processing device. Thus, use of the operation status of the device makes it possible to more appropriately select the pre-deterioration image in which no smoke has been generated.

Note that the effects described in the present description are merely examples and are not limited, and other effects may be provided.

Note that the present technology can also have the following configurations.

(1)

An information processing device comprising:

a generation unit that generates an output image by correcting a first image based on deterioration of the first image due to a substance generated during surgery estimated based on the first image that is an image regarding surgery and a second image that is an image prior to the first image.

(2)

The information processing device according to (1), wherein the generation unit corrects the first image based on deterioration of the first image due to smoke estimated based on the first image and the second image.

(3)

The information processing device according to (2), wherein the generation unit corrects the first image based on deterioration estimated based on a past first image in which no smoke is generated or the second image that is a past output image generated by the generation unit and the first image.

(4)

The information processing device according to (1), (2) or (3) further comprising:

an estimation unit that estimates deterioration of the first image due to a substance generated during the surgery based on the first image and the second image, wherein the generation unit generates an output image by correcting the first image based on an estimation result by the estimation unit.

(5)

The information processing device according to (4), wherein the estimation unit generates a converted image in which a pixel value of the first image is converted so that a histogram of the first image matches a histogram of the second image, and calculates a correction amount map based on the converted image and the first image.

(6)

The information processing device according to (5), wherein the generation unit generates the output image based on the first image and the correction amount map.

(7)

The information processing device according to (5) further comprising a motion compensation unit that estimates a motion vector based on the first image and the second image and executes motion compensation on the second image based on an estimated motion vector to align the second image, wherein the estimation unit generates a converted image in which a pixel value of the first image is converted so as to match a histogram of the aligned second image.

(8)

The information processing device according to (7) further comprising a histogram conversion unit that generates a converted image in which a pixel value of the first image is converted so that a histogram of the first image matches a histogram of the second image, wherein the motion compensation unit aligns the second image by estimating a motion vector based on the converted image and the second image, and executing motion compensation on the second image based on an estimated motion vector.

(9)

The information processing device according to (5), (6) or (7), wherein the estimation unit calculates a difference between the converted image and the first image as the correction amount map.

(10)

The information processing device according to (5), (6) or (7), wherein the estimation unit calculates the correction amount map based on a maximum pixel value among pixel values included in the first image, the converted image, and the first image.

(11)

The information processing device according to any one of (5) to (9), wherein the estimation unit further executes processing of forming the correction amount map using the first image as a guide image.

(12)

The information processing device according to (1), further comprising a selection unit that selects one of a past output image or a past first image generated by the generation unit as a second image based on an operation status of an electronic device connected to the information processing device.

(13)

A generation method, wherein a computer executes processing of generating an output image by correcting a first image based on deterioration of the first image due to a substance generated during surgery estimated based on the first image that is an image regarding surgery and a second image that is an image prior to the first image.

(14)

A generation program for causing a computer to function as a generation unit that generates an output image by correcting a first image based on deterioration of the first image due to a substance generated during surgery estimated based on the first image that is an image regarding surgery and a second image that is an image prior to the first image.

REFERENCE SIGNS LIST

10 IMAGE-CAPTURING DEVICE
11 IMAGE-CAPTURING UNIT
12, 22 COMMUNICATION UNIT
20 DEVICE USAGE MONITORING DEVICE
21 MONITORING UNIT
30 NETWORK
100 INFORMATION PROCESSING DEVICE
101*a*, 101*b* MEMORY
102 SELECTION UNIT
103, 105*a* HISTOGRAM CONVERSION UNIT
104 MOTION COMPENSATION UNIT
105 DETERIORATION ESTIMATION UNIT
105*b* CORRECTION MAP CALCULATION UNIT
105*c* CORRECTION MAP FORMATION UNIT
106 GENERATION UNIT

The invention claimed is:

1. An information processing device, comprising:
a central processing unit (CPU) configured to:
estimate, based on a first image and a second image, a deterioration of the first image due to a substance generated during a surgery, wherein
the first image is an image regarding the surgery, and the second image is an image prior to the first image;
generate a converted image in which a pixel value of the first image is converted so that a histogram of the first image matches a histogram of the second image;
calculate a correction amount map based on the converted image and the first image; and
generate an output image based on the correction amount map and a correction of the first image, wherein
the correction of the first image is based on the deterioration of the first image.

2. The information processing device according to claim 1, wherein
the CPU is further configured to correct the first image based on the deterioration of the first image due to smoke, and
the deterioration of the first image due to the smoke is estimated based on the first image and the second image.

3. The information processing device according to claim 2, wherein the second image is one of a past first image in which no smoke is generated or a past output image.

4. The information processing device according to claim 1, wherein the CPU is further configured to:
estimate a motion vector based on the converted image and the second image; and
execute a motion compensation on the second image based on the estimated motion vector to align the second image,
wherein the converted pixel value of the first image in the generated converted image matches a histogram of the aligned second image.

5. The information processing device according to claim 4. wherein the CPU is further configured to align the second image based on the estimated motion vector.

6. The information processing device according to claim 1, wherein the CPU is further configured to calculate a difference between the converted image and the first image as the correction amount map.

7. The information processing device according to claim 1, wherein the CPU is further configured to calculate the correction amount map based on a maximum pixel value among pixel values included in the first image and the converted image.

8. The information processing device according to claim 1, wherein the CPU is further configured to execute a process of a formation of the correction amount map based on the first image as a guide image.

9. The information processing device according to claim 1, wherein the CPU is further configured to select one of a past output image or a past first image as the second image based on an operation status of an electronic device connected to the information processing device.

10. A generation method, comprising:
estimating, by a central processing unit (CPU), a deterioration of a first image due to a substance generated during a surgery based on the first image and a second image, wherein the first image is an image regarding the surgery, and the second image is an image prior to the first image;

generating, by the CPU, a converted image in which a pixel value of the first image is converted so that a histogram of the first image matches a histogram of the second image;

calculating, by the CPU, a correction amount map based on the converted image and the first image; and generating, by the CPU, an output image based on the correction amount map and a correction of the first image, wherein the correction of the first image is based on the deterioration of the first image.

11. A non-transitory computer-readable medium having stored thereon, computer-executable instructions that when executed by an information processing device, causes the information processing device to execute operations, the operations comprising:

estimating, based on a first image and a second image, a deterioration of the first image due to a substance generated during a surgery, wherein the first image is an image regarding the surgery, and the second image is an image prior to the first image;

generating a converted image in which a pixel value of the first image is converted so that a histogram of the first image matches a histogram of the second image;

calculating a correction amount map based on the converted image and the first image; and generating an output image based on the correction amount map and a correction of the first image, wherein the correction of the first image is based on the deterioration of the first image.

* * * * *